United States Patent
Arbelbide et al.

(10) Patent No.: US 12,419,234 B2
(45) Date of Patent: Sep. 23, 2025

(54) AUTOMATED PRECISION POLLEN APPLICATOR FOR ROW CROPS

(71) Applicant: PIONEER HI-BRED INTERNATIONAL, INC., Johnston, IA (US)

(72) Inventors: Martin Arbelbide, Eau Claire, WI (US); Brice Floyd, West Des Moines, IA (US); Jeremy K Johnson, Roland, IA (US); Nitin Kandpal, Hyderabad (IN); Collin Lamkey, Mankato, MN (US); Manuel E Ruidiaz, Sacramento, CA (US); Alexander Sack, Hillsborough, NJ (US); Stacy Thorson, Grimes, IA (US); Jeffrey Dale Wille, Ankeny, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 236 days.

(21) Appl. No.: 18/263,810

(22) PCT Filed: Mar. 1, 2022

(86) PCT No.: PCT/US2022/070890
§ 371 (c)(1),
(2) Date: Aug. 1, 2023

(87) PCT Pub. No.: WO2022/217177
PCT Pub. Date: Oct. 13, 2022

(65) Prior Publication Data
US 2024/0306570 A1  Sep. 19, 2024

Related U.S. Application Data

(60) Provisional application No. 63/172,197, filed on Apr. 8, 2021.

(51) Int. Cl.
*A01H 1/02* (2006.01)
*A01B 69/04* (2006.01)
*G06Q 50/02* (2024.01)

(52) U.S. Cl.
CPC ........... *A01H 1/027* (2021.01); *A01B 69/008* (2013.01); *G06Q 50/02* (2013.01)

(58) Field of Classification Search
CPC ....... A01H 1/027; A01B 69/008; G06Q 50/02
(Continued)

(56) References Cited

U.S. PATENT DOCUMENTS

| 6,141,904 A | 11/2000 | Greaves et al. |
| 9,433,161 B2 | 9/2016 | Cope et al. |

(Continued)

FOREIGN PATENT DOCUMENTS

| CN | 111183776 A | 5/2020 |
| WO | 2020095290 A1 | 5/2020 |
| WO | 2021/060374 A1 | 4/2021 |

OTHER PUBLICATIONS

International Search Report and Written Opinion for International Application No. PCT/US22/70890, mailed Jul. 1, 2022.
(Continued)

*Primary Examiner* — Allen H Nguyen

(57) ABSTRACT

Automated precision applicator for row crops with dual sided applicators that can be used to direct pollen to multiple areas of the plant, as well as to measure phenotypic characteristics of plant fruiting bodies and detect successful pollination.

22 Claims, 8 Drawing Sheets

(58) Field of Classification Search
USPC .......................................................... 382/110
See application file for complete search history.

(56) References Cited

U.S. PATENT DOCUMENTS

| | | | |
|---|---|---|---|
| 9,658,201 | B2 | 5/2017 | Redden et al. |
| 9,943,049 | B2 * | 4/2018 | Safreno .................. A01H 1/027 |
| 10,175,362 | B2 | 1/2019 | Redden et al. |
| 10,761,211 | B2 | 9/2020 | Redden et al. |
| 11,445,665 | B2 | 9/2022 | Redden et al. |
| 12,367,532 | B2 * | 7/2025 | Bongartz ............. A01G 31/042 |
| 2013/0118067 | A1 | 5/2013 | Cope et al. |
| 2014/0373445 | A1 * | 12/2014 | Bangera .................. A01H 1/027 |
| | | | 47/1.01 R |
| 2021/0068335 | A1 * | 3/2021 | Noivirt-Brik .......... A01H 1/027 |
| 2021/0090274 | A1 | 3/2021 | Fu et al. |
| 2022/0000051 | A1 * | 1/2022 | Geltner .................. A01H 1/027 |
| 2022/0061243 | A1 | 3/2022 | Borrowman et al. |
| 2022/0400637 | A1 | 12/2022 | Borrowman et al. |
| 2023/0165181 | A1 * | 6/2023 | Scheiner ............. A01M 7/0089 |
| | | | 47/1.41 |
| 2024/0373777 | A1 * | 11/2024 | Postrel ................. A01B 79/005 |

OTHER PUBLICATIONS

Extended European Search Report for European Application No. EP227856101, mailed Jan. 31, 2025, 9 Pages.

* cited by examiner

AUTOMATED PRECISION POLLEN APPLICATOR FOR ROW CROPS

FIELD OF THE INVENTION

Embodiments of this invention pertain to the imaging of fruiting bodies, such as corn ears, on a live plant to detect characteristics that may be used for plant phenotyping and for automated pollination of crops such as maize. Embodiments of this invention include dual side applicators and on-board real time graphic processing that allows multiple plant fruiting bodies on a single plant to be automatically pollinated in one pass.

BACKGROUND

Plant breeders, seed producers and grain producers have a need to determine the developmental phase of plant fruit, measure their attributes, or fertilize with pollen for seed. For crops grown in rows, the upper leaves of the plant may form a canopy, obscuring the fruit or flowers from aerial viewing. Even in the absence of a plant canopy, the phenotyping and artificial pollination of plants can be time consuming and prone to human error. An additional complication is that a single plant may have multiple fruiting bodies, each of which must be pollinated.

Thus, there is a need for automated phenotyping that provides automated imaging of plant fruit or flowers not easily seen from an aerial view in order to obtain an objective and unbiased measurement of aspects of the plant, such as the height, size and location, as well as to apply pollen to the one or more fruiting bodies present on different portions of the plant.

SUMMARY OF INVENTION

Embodiments described herein involve an imaging system for identifying the location and/or other phenotypic characteristics of the plant fruit or flowers. The imaging system may assess yield, yield potential (quantity), disease and overall health. In some embodiments, the imaging system is designed to account for image distortion and poor lighting as the imaging system is transported between rows of plants. In some embodiments, the image and location of the plant flower or fruit, such as an ear in the process of silking, may be utilized to direct automated pollination of the plants. In some embodiments the plant will have two or more plant fruiting bodies, each of which may be pollinated in one pass by automated imaging and pollinating units on each side of the row of plants.

BRIEF DESCRIPTION OF THE DRAWINGS

The disclosure can be more fully understood from the following detailed description and the accompanying drawings, which form a part of this application.

DETAILED DESCRIPTION

Figure 1:
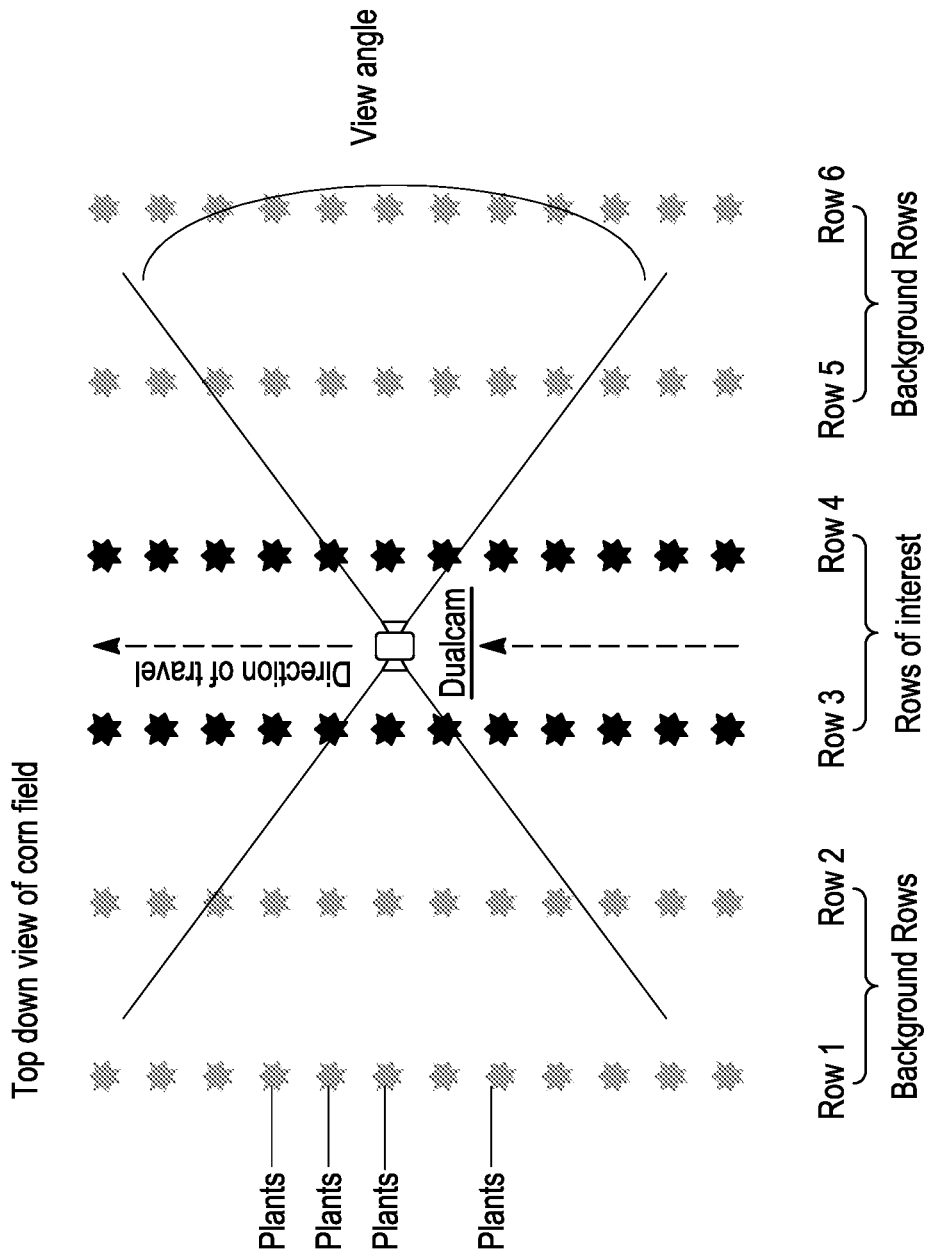
FIG. 1 provides an illustration of the orientation of the corn ear and corn silk detection device relative to the plant rows and its direction of travel through the field.

Embodiments described herein involve an imaging system for identifying the location and/or other phenotypic characteristics of the plant fruit or flowers, such as the fruiting bodies of hybrid cereal crops. Hybrid cereal crops include, but are not limited to, wheat, maize, rice, barley, oats, rye and sorghum. In one embodiment, the imaging system is transported between rows of cereal crop plants. For example, in the case of corn, corn is typically planted in rows spaced 15 to 30 inches from adjoining rows, although greater or lesser corn row spacing is also possible. Proper row spacing allows plants room to explore for nutrients and minimizes the adverse effects of competition from neighboring plants. In Iowa, and in most regions of the midwest, 20 inches and 30 inches are the most common row spacing configurations.

Accordingly, with typical spacing, an imaging system transported between the rows would be about 15 inches from the row of corn plants on each side, which tends to result in a limited field of view when a standard camera lens is used. Additional difficulties for imaging corn ears arise as a result of low or inconsistent lighting conditions that can be caused by clouds, time of day or night, the canopy formed by the uppermost leaves of the plant, by other leaves that obscure the camera's view of the corn ear and its silks, by the need to image multiple ears of corn, and by movement of the camera as it is transported between the rows.

In one embodiment, a semi-hemispherical lens is used to provide an adequate field of view to identify one or more fruiting bodies on a plant. However, this lens causes significant distortion of the image which makes it especially difficult to determine the ear height and location of the fruiting bodies. To overcome this distortion, the image is flattened, followed by object recognition within the image. In order to use such flattened image to distinguish the plant fruiting body from the leaves, stem and other plant parts, and corn ear identification such image flattening and recognition must occur in real time. Accordingly, in some embodiments, an on-board image processing device is utilized for immediate recognition and location of the plant fruiting body.

Such image processing may be further complicated by the fact that plant fruiting bodies may be obscured by leaves or other plant parts. In some cases, the plant fruiting bodies may not be visible from one side of the row. Accordingly, a dual camera system has been developed, wherein a boom is used to position a camera on each side of a row (see FIGS. 1, 2, 3, and 8). The image from each camera opposite a corn plant is utilized to detect a corn ear and/or silks and associated with an x, y and optionally z coordinate position. Such coordinates may be utilized to direct an automated pollination sprayer to the location of the corn ear and silk. A GPS system, and optionally an inertial measurement unit (IMU), may be associated with the camera on each side of the row to determine these coordinates. The known height of the camera on the transport device on which it is mounted may also be used for coordinate determination.

One embodiment is a multi-row camera system. Each camera in each row will have a left and right camera, and there may further be a plurality of such camera systems across several rows. The camera may be mounted on a transport device that fits between the rows, or may be suspended from a boom (see FIG. 8) that allows the camera to be positioned under the canopy in a position suitable for imaging corn ears. Transport devices include, but are not limited to, robotic vehicles (such as those produced by Boston Dynamics and NAIO Technologies), tractors, and drones.

The imaging system may further assess plant characteristics such as yield, yield potential (quantity), disease and overall health. The image and location of the plant flower or fruit, such as an ear in the process of silking, may be utilized to direct automated pollination of the plants. In this embodiment, the location information from the imaging device would be utilized to direct a pollen application device to deliver pollen to the corn ear silks. The imaging permits a precise application of pollen that results in less waste and a more efficient pollen application that leads to improved seed set.

FIG. 1 provides an illustration of a corn ear and corn silk detection device moving through the field parallel to rows. In this embodiment, the cameras are oriented at approximately 90 degrees to the left or right of the direction of travel, although any known angle of orientation may be used. The camera detects objects in the plant rows closest to the imaging and detection system with a high degree of probability, while background and off target rows have a lower probability of object detection due to their distance from the system that results in reduced target size as well as a greater image distortion and shrinkage of distant objects relative to the closest rows. Therefore, with a one camera one row system, fruiting bodies occurring in the background have a greater potential to be missed by the image recognition software, and the second (or additional) fruiting bodies on a row crop plant commonly occurs in a distally related part of the plant.

For example, in corn plants with a second ear, the second ear is commonly located a few nodes from the first ear and oriented at a rotational axis of 90 to 180 degrees on the stalk and positioned lower on the plant, and therefore deeper in the canopy where pollen may not adequately shed. While dual ear corn often doesn't result in a significant grain yield increase when it does occur in hybrid grain production, some inbred varieties with proper spacing and growing conditions may be managed in a way to optimize the production of a second ear. In the past this is not done in the regular course of seed production due to the difficulty of obtaining sufficient seed yield on the second ear. However, this invention, by assuring that the second ear receives sufficient pollen, serves as a potential enabler of dual ear seed production. This can be of value in seed production, especially when seed quantities are low, such as when inbred breeder seed is scarce and every seed is needed for plant propagation and seed multiplication.

Figure 2:
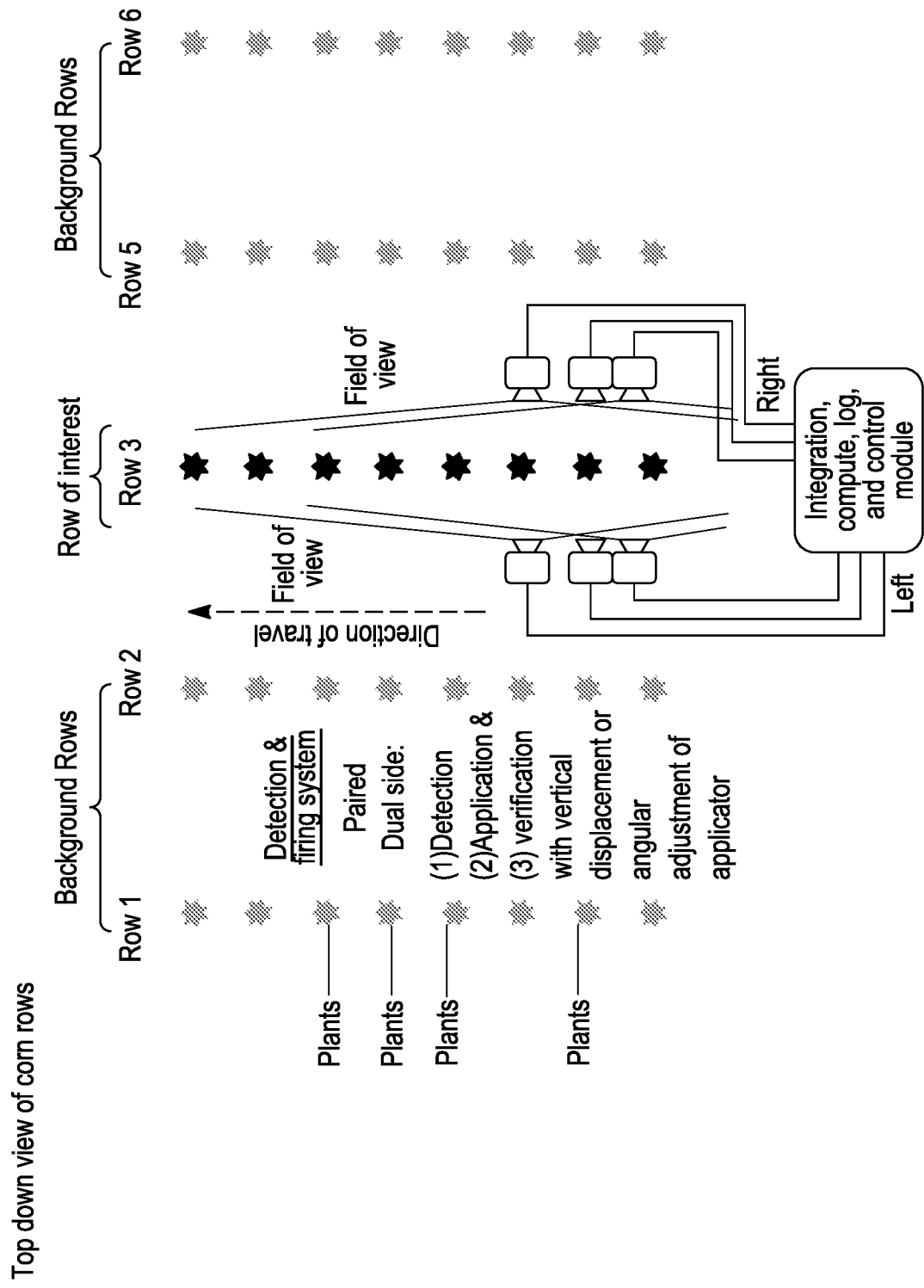
FIG. 2 provides an illustration of a dual side imaging system.
Figure 3:
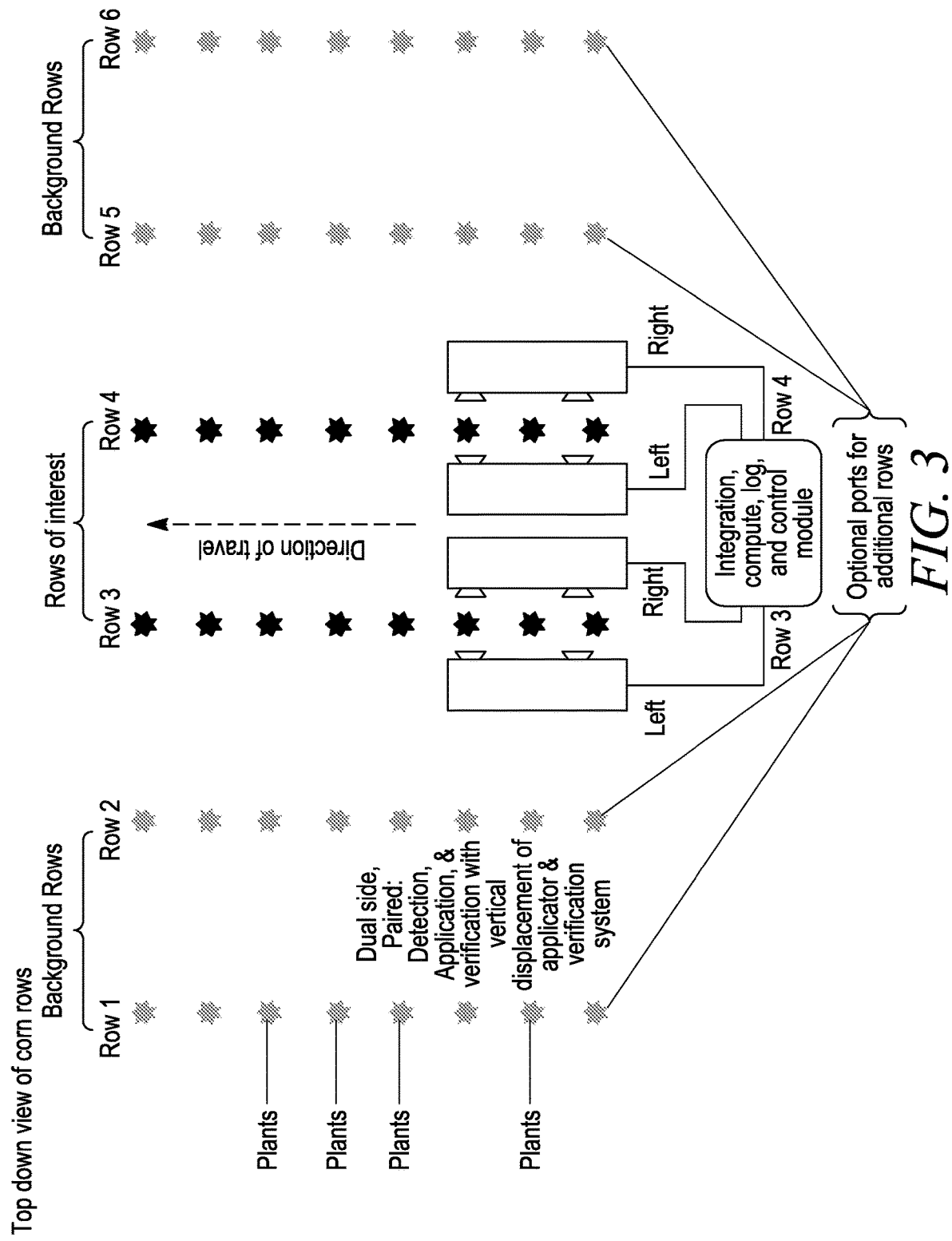
FIG. 3 further illustrates a dual side imaging system in a multi-row embodiment.

To help achieve maximum seed production for dual ear corn plants, the dual side imaging system was developed, as illustrated in FIGS. 2 and 3. FIG. 3 is similar to FIG. 2 and further illustrates a multi-row embodiment comprising both a left and right-side imaging and pollination unit in-between the interior rows. This system may be used for other row crops which comprise multiple fruiting bodies, such as for wheat with a main stem and one or more tiller stems, as well as for crops such as rice, barley, oats, rye and sorghum.

Image Capture and Processing

Figure 4:
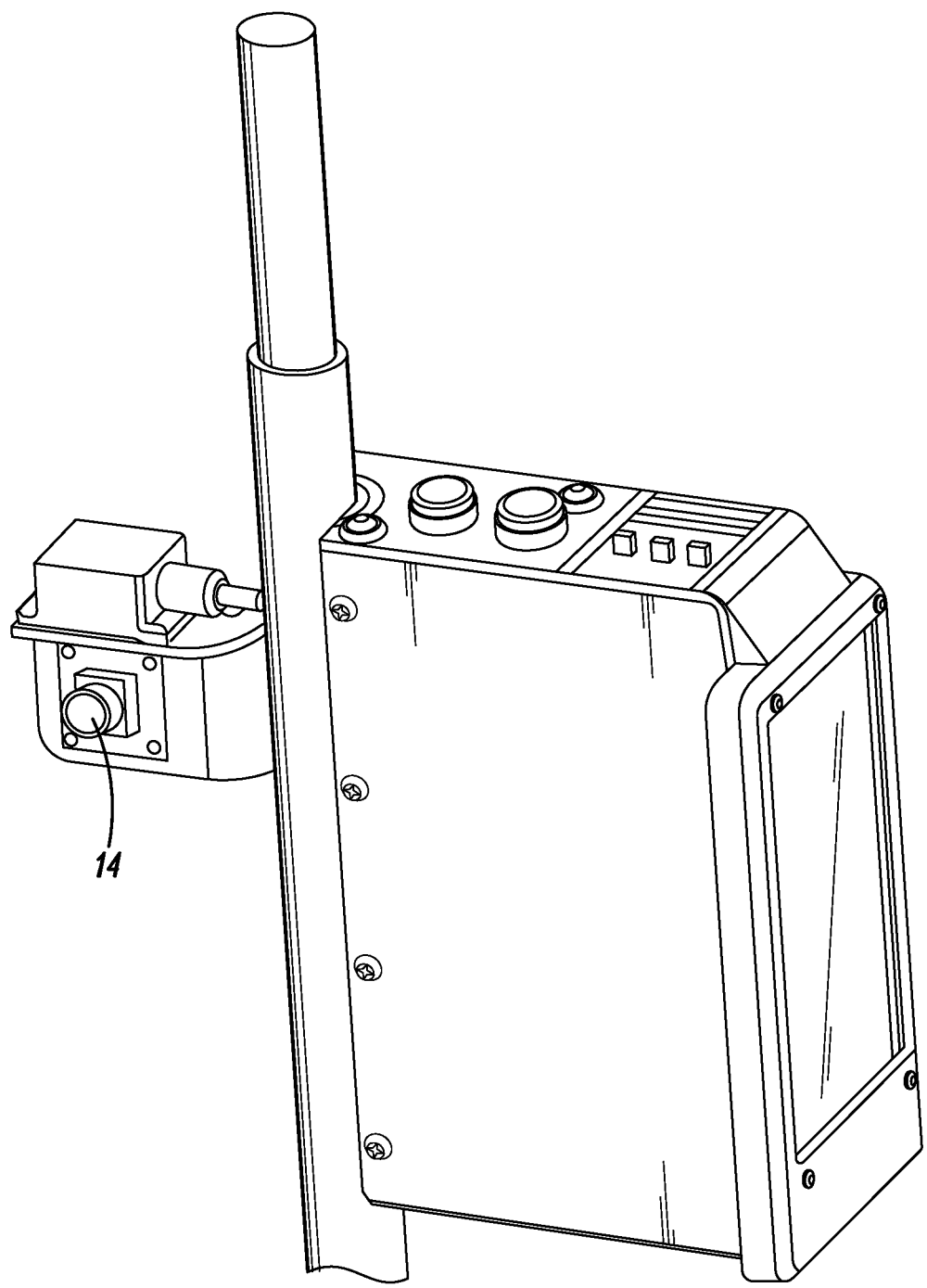
FIG. 4 provides an illustration of one embodiment of a camera with a semi-hemispherical lens.

Images are captured with a semi-hemispherical lens (14) as shown in FIG. 4. The lens feeds images into an on-board imaging system that processes the distorted hemispherical images into flattened and corrected images with identified plant reproductive parts, such as corn ears or silks, together with 3-dimensional location information sufficient to direct a pollinating device to the location of the plant reproductive part. An optional second camera may be used to direct the pollinating portion of the device to the plant reproductive part.

The images may be captured at a suitable rate for the speed of the activity. In the image capture device described in more detail below, rates of image capture of up to 30 frames per second were achieved using an NVIDIA graphics card. One graphics card per imaging device was used, although it is also possible to feed the images from two or more imaging devices into a single graphics card, which may be preferable when a 360-degree view of an individual plant or row of plants is desired. Positional data associated with the images from the dual cameras on each side of a row may be used to construct a series of photos of the plant that represent a nearly 360-degree view of the individual plant or row of plants, and the graphics card and data structure may be optimized for this task. Following image capture, raw hemi-spherical images are flattened (e.g. using open CV software to determine the camera's intrinsic matrix and distortion coefficients model) and, in embodiments with an inertia measurement unit (IMU), adjusted based on camera angle which can change as the device moves across land. In some embodiments, such as a boom mounted system (see FIG. 8), an IMU may not be needed because the boom is relatively parallel to the ground. However, with the field gimbal-free system, the transport of the camera through the field causes the capture of images not consistently aligned on the x, y and z planes, resulting in warped images and incorrect ear height measurements. To correct this problem, further image adjustment was needed, and in some embodiments an IMU was added above the camera. For example, in certain experiments images were taken at a slight right-ward angle and IMU measurements were used to correct the right-ward angle in order to obtain a corrected perspective image directly perpendicular to the target object. Images were undistorted (flattened) with pre-calibrated parameters (K,D and FoV Scale) and then a perspective warp was applied to straighten the image using inertial measurement unit data. Following flattening and straightening, pixels were counted and height, distance and/or area were computed based on known pixel dimensions to allow measurement of vertical height of ears and silks as well as an assessment of depth. To enhance the speed of the calculation and facilitate on board processing, images may be scaled down from the full resolution image.

In some embodiments a laser distance sensor (or ultrasonic sensor, lidar, multidimensional camera or radar) may be used to detect distance to stalks, and optionally, to determine distance to ground. The latter may be particularly useful on boom mounted systems.

When objects were measured in a non-IMU embodiment, the video frame extracted from video was undistorted from a hemi-spherical view to a flattened view using an undistortion matrix (camera model) for that particular sensor. An object detection model was then used to identify an object of interest from within the video frame. The pixel coordinates of the detections centroid or bounds of that detection were recorded. Measurement of the object height used a combination of the pixel coordinates and a camera's intrinsic matrix. The center of the image collected was the same as the mounting height of the camera. Measuring objects away from the center of the camera view required adding (for higher objects from center) or subtracting (for lower objects from center) a calibrated distance which is calculated from the camera's intrinsic matrix associated with the specific camera and the objects distance from the camera (or depth) is used as a multiplier. This process was done for each frame of a video.

When objects were measured in an embodiment comprising an IMU, useful when there would be significant variation from a horizontal plane, the video frame extracted from video was undistorted from a hemi-spherical view to a flattened view using an undistortion matrix for that particular sensor and/or camera model. The IMU was used to correct for variable camera angles encountered when operating the system by measuring the camera orientation in space relative to an artificial horizon. Pitch, roll, and yaw measurements from the IMU were used in Euler equations to warp the perspective of the image back to a nominally positioned camera as if it was level to the horizon and perpendicular to the target object. An object detection model was used to identify an object of interest. The pixel coordinates of the detections centroid or bounds of that detection were recorded, and a flattened image matrix model was used to convert pixel coordinates to real world measurements. This process was done for each frame of the video. This may be done either during or post video collection for determining ear or tiller height, potential yield or other plant characteristics, but must be done during video collection for use in directing automated pollination.

In other embodiments the cameras or IMUs that are associated with another transport device such as a robotic vehicle (such as those produced by Boston Dyanamics or NAIO Technologies), tractors and drones can be used through an application program interface (API) rather than adding additional camera sensors. Onboard computation may also be used for the processing of imagery through an API as well, obviating the need to add additional hardware resources.

Attributing Imagery to Specific Field Positions

A series of GNSS points were collected, with each point representing the geographic coordinates of where the image was taken by the imaging system. In one embodiment, using GPS described herein, several images were tagged with the same GPS position since the GPS system took about 10 positions per second, and the imaging system took about 30 frames per second. A box image was created with a series of boxes, with each box representing a 17 foot long row of corn with a width of 30 inches and a point representing the location of the camera when each image was taken.

Lighting

Natural lighting was utilized. However, artificial lighting may also be utilized to assist in non-daylight hours when phenotyping and/or pollination is needed. Ultraviolet or infrared lighting or thermal imaging may be utilized to enhance illumination of the corn silks, flowers, or other plant parts. While the camera may have some level of automatic gain and exposure to enhance imaging in low light conditions, this can also result in motion blur. To remedy this, the exposure can be limited to a threshold value and then gain may be used, or an external sensor can be used to adjust exposure and lighting.

Identifying Ears and Silks with Trained Models

Videos were collected in a number of corn fields during different stages of physiological growth stage and environmental lighting conditions. A training set was created from the videos and flattened and corrected images were generated.

Figure 5:
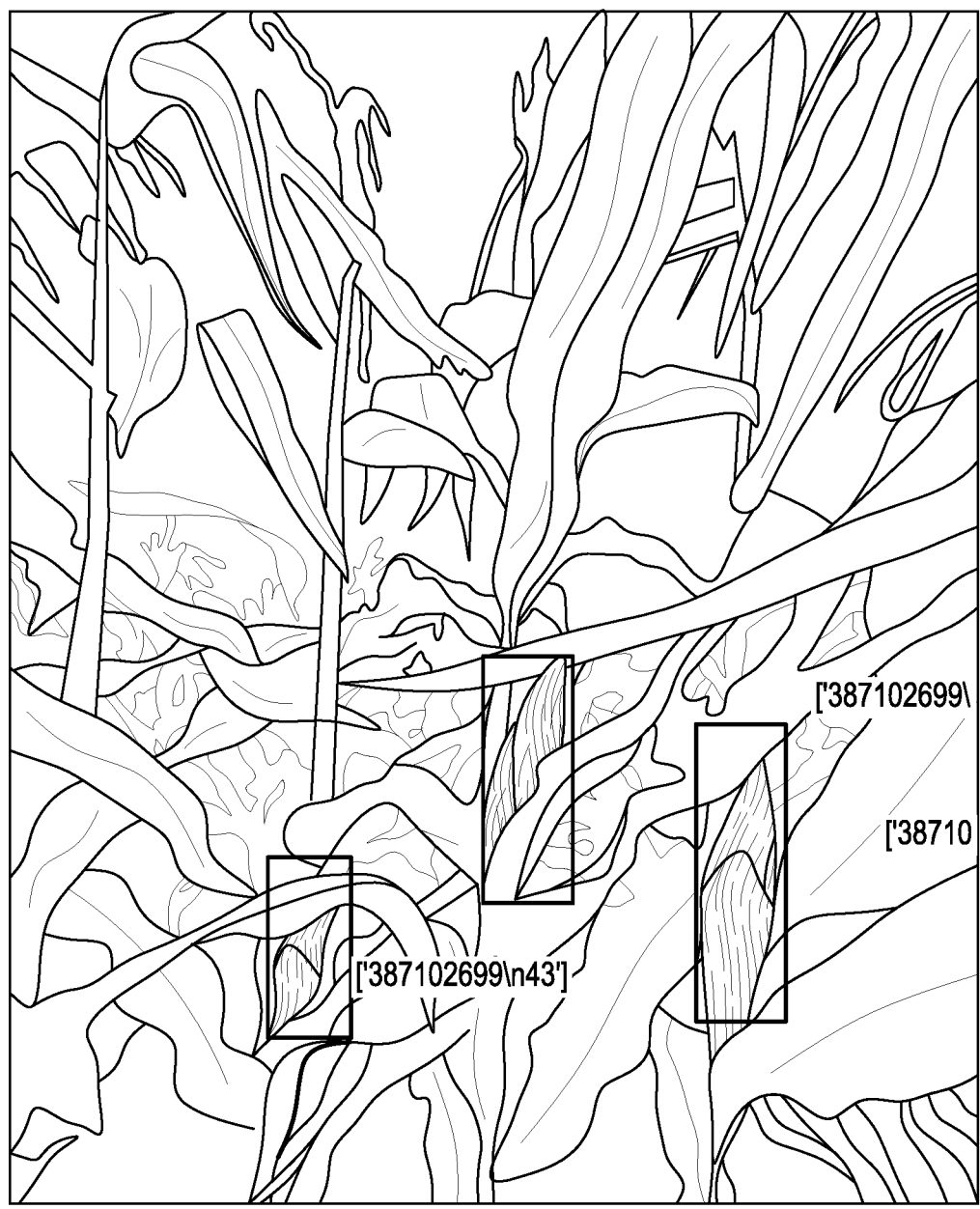
FIG. 5 illustrates an in-field example of the detection of a corn ear and measurement of corn ear height using the imaging system via a side-facing camera mounted to an inter-row implement.
Figure 6:
FIG. 6 illustrates an in-field example of the detection of corn silks using the imaging system via a forward-facing camera mounted to a human walking inter-row.

Approximately 18,000 images were labeled by tracing a square polygon around pixels associated with corn ear objects, as is shown in FIG. 5. Labeled (also called annotated) imagery was then passed through a convolutional neural network, building an object detection tool from imagery. Accuracy of detections was then evaluated using imagery from corn fields not included in the model training set and quantifying missed or incorrectly labeled objects. An identical process was done for the detection of corn silks, as shown in FIG. 6, where individual silks were traced out using a square and an identical detection training and validation was applied.

Images taken at about 30 frames per second will show the same ear across several images, so the system tracks continuity of the ear (or other plant reproductive part) throughout the various images. One embodiment that may be utilized to achieve this continuity of image is to locate plant reproductive part relative to the center point of the image.

Measuring (Height)

Images were taken of fixed height objects in order to correlate the height of objects in the raw image with those in a flattened and corrected image.

The application of the flattening and correction noted above, as well as accounting for the elevation of the camera when there was vertical displacement, resulted in highly accurate measurements with an average error of only 0.65 inches. In contrast, this was significantly more accurate than when a non-specific, generic camera intrinsic matrix and distortion coefficient was used, since the average error of the measurements using the generic intrinsic matrix was 6.23 inches on the same objects.

Distance Assumption Between Camera and Ear, Silk or Fruiting Body.

In order to measure the height of a detected object the distance between the camera and the object of interest must be known. For the embodiments designed for corn, a 15-inch depth of field was used based on a standard plant row spacing of 30 inches. This distance assumption would be adjusted for the plant row spacing used. Some camera movement also occurred since the camera was not always positioned in the center of the alley equally between the two rows. Modification of this distance assumption also requires tuning the camera intrinsic matrix and distortion coefficients model to the specific desired distance.

In other embodiments, a system for camera stabilization such as camera gimbals or gyroscopic stabilizers may be added to maintain a stable camera position in 3D space while the transport system moves through the scene. The camera drifting off center of the inter-row space or varying in its angles of view may be affected by either the irregular soil surface the camera is being moved along upon, or thorough other leaning of drifting of the apparatus. A gimbal or related stabilizer could be used to alleviate such manipulation of the camera position.

Directing a Pollen Applicator

Various options exist for an automated pollen applicator, for example, once the ear, silk or plant fruiting body is identified and the location determined, a robotic arm can be used to direct a pollinating nozzle or spray tube.

Figure 7:
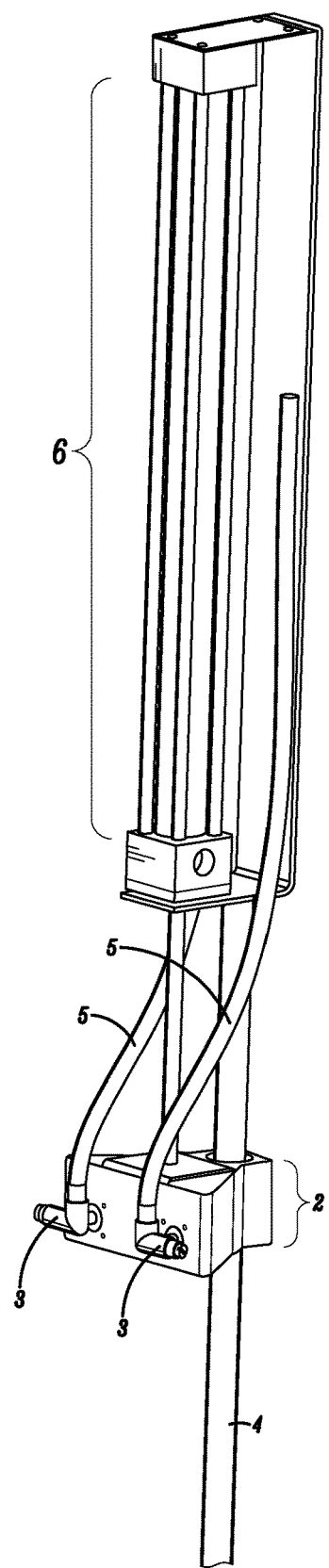
FIG. 7 illustrates an embodiment of a pollen applicator with a vertical adjustment and pivoting dual spray heads.
Figure 8:
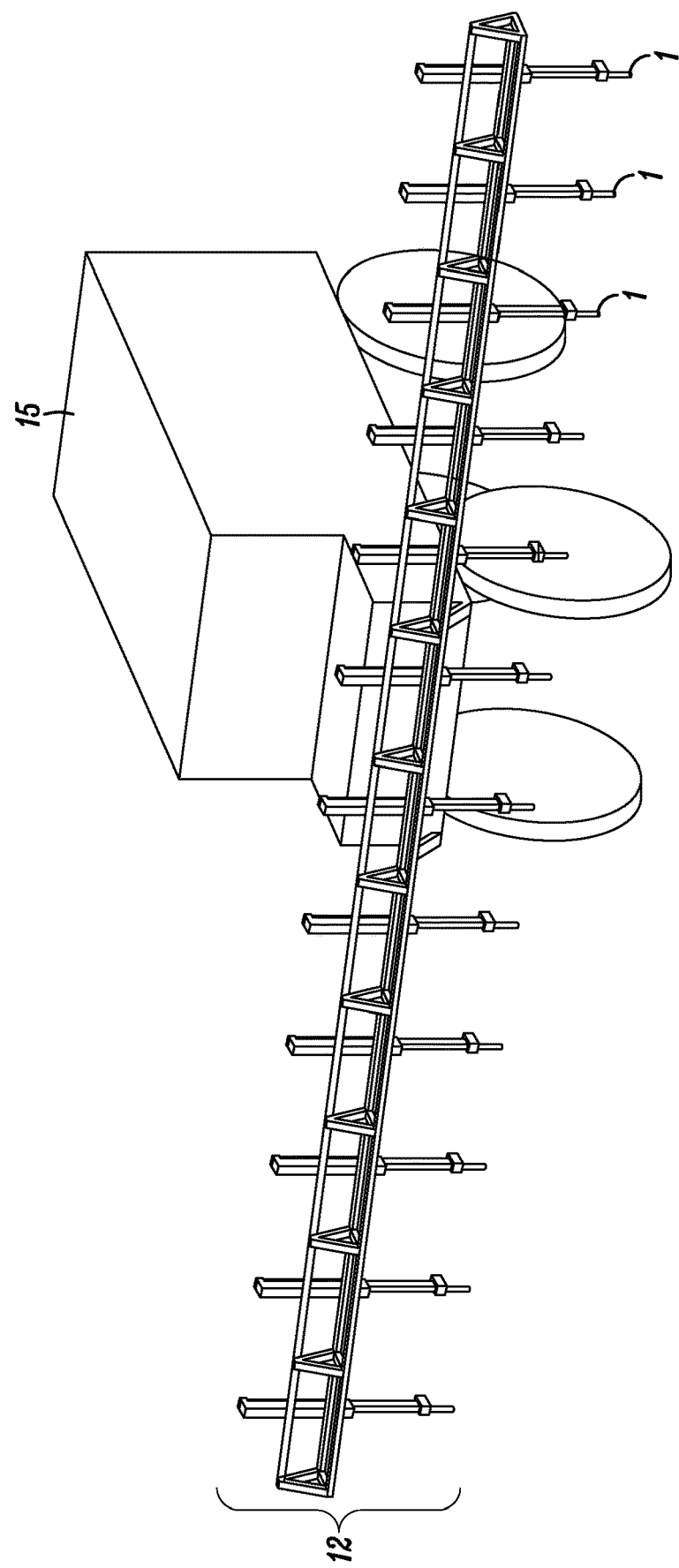
FIG. 8 illustrates an embodiment of an array of pollen applicators boom mounted on a transport device.

One embodiment of a pollen applicator was designed as shown in FIGS. 7 and 8. This pollen applicator is boom (12)

mounted on a transport device (15) (as shown in FIG. 8) and comprises a series of spray units (1). FIG. 7 shows a close up of an individual spray unit, which comprises a sliding spray block (2) powered by a hydraulic lift (6) that can be rapidly raised and lowered along slide rail (4). The range of vertical motion may be between 10 and 40 inches, likely centered around 24 inches. The spray block (2) comprises two nozzles (3), each connected to a pollen transport tube (5) and in one embodiment, each nozzle is independently activated by a rotary servomotor inside the spray block (2) that allows for precise control of angular position and direction of pollen spray. This allows for precise elevation control and angle of spray, up to 90 degrees of rotation either up or down from the horizontal plane, so that the pollen applicator on each side of the row of a plant with multiple plant reproductive parts can precisely spray each flower or silk. In the case of corn, the top down orientation is especially beneficial to direct the spray nozzle to the approximate height of the second ear, where the spray can be directed to the silks without being blocked by the upper leaves of the plant.

Determining if/when to Spray Pollen

A second camera may then be used to direct the pollen applicator more specifically to the plant reproductive part, and may be used to confirm application of the pollen to the silk as well. The same type of camera, image processing and image recognition software may be used, or alternately, a standard camera lens with less curvature and need for image processing may be used. To account for the latency between the lead set of cameras and the pollen applicator, the lead set of cameras may be physically positioned in front of pollen applicator by some distance to allow time for image processing. A lead camera distance of about 3 feet will allow for sufficient latency time when the machine is traveling at 5 mile per hour. An ethernet or USB camera may be used to avoid signal delay. Colorant and/or fluorescent dye may be added to the pollen for verification and to enhance image verification of pollination.

Phenotyping and Characterization Applications

In addition, the device and methods described herein may be used to phenotype or characterize plants. For example, with corn, a GPS heat map of silk density and distribution may be generated, corn silks may be counted, 5%, 50%, 75% and/or 100% flowering time may be estimated, stem size can be measured or lodging resistance estimated, ear size and diameter may be measured and grain yield can be estimated. The device and methods can also be utilized to count total primary ears, total secondary ears, and/or total ears. Likewise for wheat, the total number of primary spikes, total number of tillers, and/or total number of wheat seed heads may be counted.

While the invention has been particularly shown and described with reference to a preferred embodiment and various alternate embodiments, it will be understood by persons skilled in the relevant art that various changes in form and details can be made therein without departing from the spirit and scope of the invention. For instance, while particular examples may illustrate the methods and embodiments described herein using corn, the principles in these examples may be applied to any plant. Therefore, it will be appreciated that the scope of this invention is encompassed by the embodiments of the inventions recited herein and in the specification rather than the specific examples that are exemplified below.

We claim:

1. A method for automated pollination of row crop plants with multiple plant reproductive structures from a transport device moving through the row of plants, said transport device comprising two or more pollinating units positioned under the plant canopy and between two rows of plants, each pollinating unit comprising a first pollinating device and first imaging device directed to a first row of plants on a left side of the pollinating unit, and a second pollinating device and a second imaging device directed to a second row of plants on a right side of the pollinating unit, wherein the first pollinating device and second pollinating device are each capable of directing pollen to a plurality of locations on a plant, the method comprising taking a plurality of images of plants on both sides of the pollinating unit, processing the plurality of images on said transport device to identify a pixel pattern in each image indicative of one or more plant reproductive structures on the plant, determining the 3-dimensional spatial position of the identified one or more plant reproductive structures, and directing the first pollinating device and the second pollinating device to each apply pollen to the plant reproductive structures on the plants on each side of the pollinating unit.

2. The method of claim 1, wherein the imaging devices comprise a convex lens capable of approximately 180 degree field of view coverage, and the image processing comprises flattening each image.

3. The method of claim 1, wherein the image from a first pollinating unit and a second pollinating unit are combined in an image processing program to identify individual plants comprising multiple plant reproductive structures.

4. The method of claim 1, wherein identified plant reproductive structures are recorded by GPS location.

5. The method of claim 1, wherein the plant is a hybrid cereal crop.

6. The method of claim 5, wherein the cereal crop is maize, and the plant reproductive structure is at least one of a corn ear or a corn silk.

7. The method of claim 5, wherein the cereal crop is wheat, and the one or more plant reproductive structures are wheat seed heads.

8. The method of claim 1, wherein the imaging device further comprises an inertial measurement unit used to determine camera angle at the time the image is taken.

9. The method of claim 1, further comprising determining the height of each plant reproductive structures.

10. The method of claim 1, wherein each imaging unit is positioned ahead of the pollinating device based on the direction of travel of the transport device.

11. The method of claim 1, wherein an auxiliary imaging device is positioned proximal to each pollinating device and used to confirm the positioning of the pollinating devices relative to the plant reproductive structure.

12. The method of claim 1, wherein the pollinating unit further comprises a light source that preferentially illuminates the plant reproductive structure.

13. The method of claim 12, wherein the light source is ultraviolet, and the imaging device is capable of detecting ultraviolet light.

14. A method for determining the height of a plant or plant fruiting body, said method comprising taking a plurality of images of the plants, associating a camera angle with each image, flattening and correcting each image, and processing the plurality of images to identify a pixel pattern in each image indicative of the plant or plant fruiting body, and determining the height of the plant or plant fruiting body relative to a base of the plant.

15. The method of claim 14, wherein the image of the plant fruiting body is analyzed by image recognition software that determines the growth stage of the plant fruiting body.

16. The method of claim 14, wherein the plant fruiting body is a corn ear.

17. A machine for pollinating row crop plants with multiple plant reproductive structures, said machine comprising two or more pollinating units positioned under the plant canopy and between two rows of plants, each pollinating unit comprising a first pollinating device and first imaging device directed to a first row of plants on a left side of the pollinating unit, and a second pollinating device and a second imaging device directed to a second row of plants on a right side of the pollinating unit, wherein each imaging device is positioned in the direction of travel ahead of the pollinating device and wherein the first pollinating device and the second pollinating device are each capable of directing pollen to a plurality of locations on a plant.

18. The machine of claim 17, further comprising an auxiliary imaging device positioned proximal to each pollinating device and used to determine the positioning of the pollinating devices relative to the plant reproductive structure.

19. The machine of claim 18, wherein the auxiliary imaging device detects a colorant or fluorescent dye that has been added to the pollen.

20. The machine of claim 17, wherein each imaging device comprises a convex lens with a field of view ranging from 100 degrees to 250 degrees.

21. The machine of claim 17, further comprising an ultraviolet light.

22. The machine of claim 17, further comprising an image processor that determines the height of each plant reproductive part, and independently directs the first pollinating device to the height needed to pollinate the plant reproductive part on the first side of the plant, and the second pollinating device to the height needed to pollinate the plant reproductive part on the second side of the plant.

* * * * *